United States Patent
Hawkins

Patent Number: 6,057,455
Date of Patent: May 2, 2000

[54] PREPARATION OF INTERMEDIATES USEFUL IN THE SYNTHESIS OF QUINOLINE ANTIBIOTICS

[75] Inventor: Joel M. Hawkins, Old Lyme, Conn.

[73] Assignee: Pfizer, Inc., New York, N.Y.

[21] Appl. No.: 08/888,519

[22] Filed: Jul. 7, 1997

Related U.S. Application Data

[60] Provisional application No. 60/021,049, Jul. 9, 1996.

[51] Int. Cl.[7] ........................ C07D 209/52; C07C 211/00
[52] U.S. Cl. .......................... 548/452; 564/282; 564/291
[58] Field of Search ............................................... 548/452

[56] References Cited

U.S. PATENT DOCUMENTS

| | | | |
|---|---|---|---|
| 5,256,791 | 10/1993 | Braish | 548/452 |
| 5,298,629 | 3/1994 | Braish | 548/452 |

*Primary Examiner*—Alan L. Rotman
*Attorney, Agent, or Firm*—Peter C. Richardson; Paul H. Ginsburg; Mark Dryer

[57] ABSTRACT

A process for preparing a compound of the formula

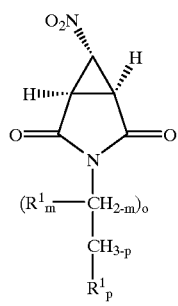

(III)

wherein $R^1$, m, o and p are described below, which comprises adding a base of the formula

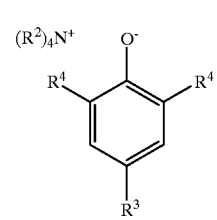

(IV)

wherein $R^2$, $R^3$ and $R^4$ are as described below, to a solution comprising a compound of the formula

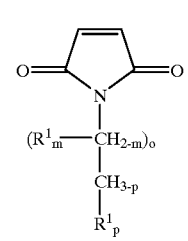

II wherein $R^1$, m, o and p are as described below, and a halonitromethane of the formula $O_2NCH_2X$, wherein X is a halogen atom dissolved in a non-aqueous inert solvent. The compounds of formula III are useful as intermediates in the syntheses of azabicyclo quinoline carboxylic acids, and their pharmaceutically acceptable salts and prodrugs, having antibacterial activity. This invention also relates to the base of formula IV wherein each $R^2$ is butyl, $R^3$ is hydrogen and each $R^4$ is t-butyl.

13 Claims, No Drawings

PREPARATION OF INTERMEDIATES USEFUL IN THE SYNTHESIS OF QUINOLINE ANTIBIOTICS

CROSS-REFERENCE TO RELATED APPLICATION

This application is a nonprovisional application claiming benefit of U.S. provisional application 60/021,049 filed Jul. 9, 1996.

BACKGROUND OF THE INVENTION

This invention relates to the antibiotic trovafloxacin having the formula

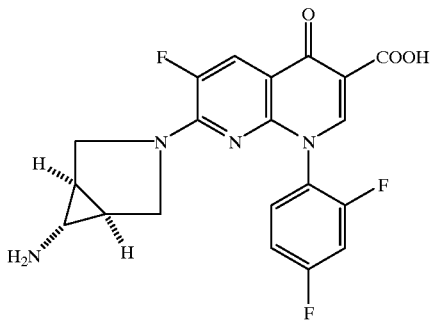

(I)

and its pharmaceutically acceptable salts and prodrugs (hereafter "the active compounds"). More particularly, it relates to a process and compositions useful in the the preparation of compounds of the formula

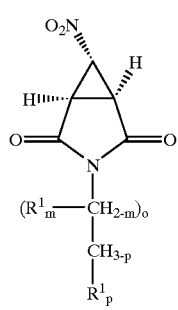

(III)

wherein $R^1$, m, o and p are as described below. The compounds of formula III are intermediates in the preparation of the compound of formula I and the pharmaceutically acceptable salts and prodrugs thereof. The antibacterial activity of the aforementioned antibiotic is described in U.S. Pat. No. 5,164,402 (the '402 patent) and U.S. Pat. No. 5,229,396 (the 396' patent) issued Nov. 17, 1992 and Jul. 20, 1993, respectively, the disclosures of which are incorporated herein, by reference, in their entirety. The foregoing patents are assigned in common with the present application.

U.S. Pat. No. 5,256,791 (the '791 patent), issued Oct. 26, 1993, describes a process, for preparing a compound of formula III by adding a base to a solution of a compound of the formula II, described below, and a nitrohalomethane, described below, in an inert, non-aqueous solvent wherein the base consists of 1,8-diazabyclo-[5.4.0]undec-7-ene (DBU) and U.S. patent application Ser. No. 08/181,942 (the '942 application), filed Jan. 18, 1994, describes the use of dimethyltetrahydropyrimidine (DMTHP) as the base in a similar process. The foregoing references are assigned in common with the present application and are incorporated herein, in their entirety, by reference.

The methods by which the compounds of formula III may be converted into the compound of formula I are set forth in detail in the aforementioned '791 patent.

SUMMARY OF THE INVENTION

The present invention relates to a process for preparing a compound of the formula

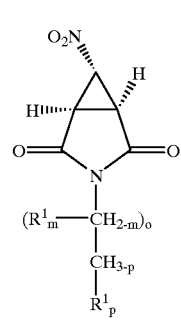

(III)

wherein each $R^1$ is independently selected from hydrogen, optionally substituted $(C_1-C_6)$alkyl or optionally substituted $(C_6-C_{10})$aryl wherein said substituents independently are attached to the maximum allowable number of carbon atoms and are each independently selected from halo, nitro, $(C_1-C_6)$ alkyl, $(C_1-C_6)$ alkoxy, amino and trifluoromethyl or two $R^1$ groups together with the carbon atom tto which they are attached form a $(C_3-C_8)$cycloalkyl ring, o is 0 or an integer from 1 to 5;

m is 0, 1 or 2; and p is 0 or an integer from 1 to 3;

which comprises adding a base of the formula

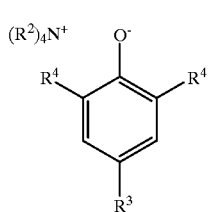

(IV)

wherein each $R^2$ may be different and is independently selected from the group comprising $(C_1-C_{16})$alkyl and benzyl;

$R^3$ is selected from the group described for $R^1$; and each $R^4$ may be different and is independently selected from $(C_1-C_6)$alkyl wherein said alkyl group may be a straight chained hydrocarbyl group or, if consisting of more than two carbon atoms may also be branched or cyclic; to a solution comprising a compound of the formula

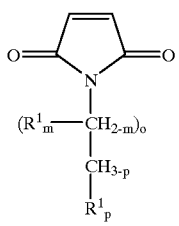

(II)

wherein $R^1$, m, o and p are as described above, and a halonitromethane of the formula $O_2NCH_2X$, wherein X is a halogen atom, dissolved in a non-aqueous inert solvent. Preferably, at least one $R^4$ is a branched $(C_4–C_6)$alkyl group. Most preferably, both $R^4$ groups are the same.

This invention also relates to a compound having the formula

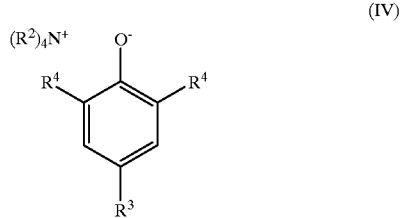

(IV)

wherein $R^2$, $R^3$ and $R^4$ are as described above with the proviso that $R^3$ cannot be hydrogen or $CF_3$ when each $R^2$ is methyl and each $R^4$ is t-butyl. Preferably, each $R^4$ is t-butyl, each $R^2$ is butyl and $R^3$ is hydrogen.

The term "halo", as used herein, refers to chloro, fluoro, bromo or iodo.

The term "alkyl" as used herein refers to straight and, if comprised of more than two carbon atoms, cyclic and branched hydrocarbyl chain and combinations thereof.

DETAILED DESCRIPTION OF THE INVENTION

The process of the present invention is illustrated in the following reaction scheme. Except where otherwise indicated, in the reaction scheme and discussion that follow, formulas I, II, III, IV and V substituents X, $R^1$, $R^2$, $R^3$ and $R^4$ are defined as above.

SCHEME

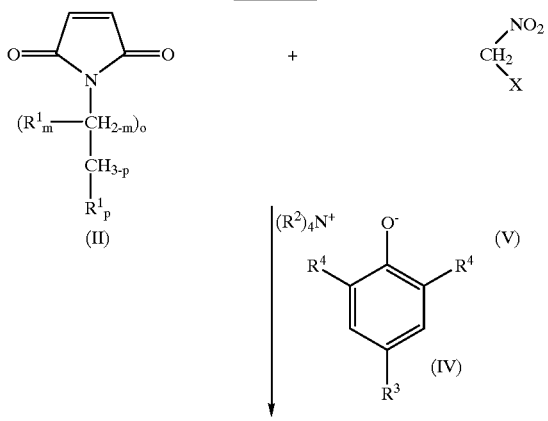

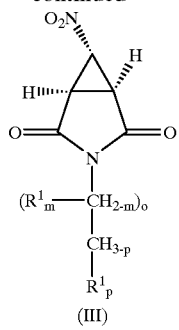

(III)

The above reaction scheme illustrates the preparation of the compound of formula III, which is a useful intermediate in the synthesis of the antibiotics, of the formula I, referred to above.

Referring to the above scheme, the compound of formula II is reacted with a halonitromethane V, preferably chloronitromethane ($O_2NCH_2Cl$) or bromonitromethane ($O_2NCH_2Br$), in the presence of the base of the formula IV to yield the compound of formula III. The base is, preferably, tetrabutylammonium 2,6-di-t-butylphenoxide. The reaction is generally effected by dissolving the compound of formula II and the halonitromethane V in a non-aqueous inert solvent and atmosphere and adding the base to the resulting solution. The reaction is, preferably, effected in the presence of a solid support material such as molecular sieves, which are believed to function by absorbing water, and diatomaceous earth, e.g., Celite (trademark), which is believed to function by absorbing undesired byproducts and facilitate filtration and mixtures thereof. Most preferably, the reaction is effected in the presence of a solid support consisting of a mixture of molecular sieves and Celite. Most preferably, the molecular sieves are used in the form of beads. Although a theory has been proposed as to how the solid supports function the invention does not depend on the validity of the theory. Inert solvents useful in the practice of the invention include, e.g., polar, aprotic solvents such as dimethylformamide (DMF), dimethylsulfoxide (DMSO) or dimethylacetamide (DMAC); ethers such as ethyl ether, glyme or tetrahydrofuran (THF) and aromatic solvents such as optionally halogenated benzene or toluene and mixtures thereof. Toluene is the preferred solvent. Suitable reaction temperatures range from about –78° C. to about 80° C., preferably from about –17 to –19° C. Compounds of the formulae II and V may be obtained commercially or can be prepared by known methods. The compound of formula IV can, generally, be prepared by treatment of the corresponding phenols with tetralkylammonium hydroxides of the formula $(R^2)_4N^+OH^-$. (See, e.g., Medebielle, M., et al. *J. Am. Chem. Soc.,* 1991, 113, 6872.) The phenols may be used neat or dissolved in a non-aqueous solvent such as those described above for use in dissolving the mixture of compounds II and V, a $(C_1–C_6)$ alkanol or acetonitrile. The preferred solvent is toluene. The reaction is run at a temperature of from about –50 to about 50° C., preferably at room temperature, for a period of from about 5 minutes to two hours. The solvent is removed from the reaction mixture by evaporation, preferably under vacuum, optionally followed by the addition and evaporation of solvents such as toluene to aid in drying. The compounds of formula IV are used without further preparation.

The procedures by which compounds of the formula III may be used to prepare the compound of formula I, related azabicyclo quinoline carboxylic acids and their pharmaceutically acceptable salts and prodrugs thereof are set forth in the '791 patent referred to above and incorporated herein, in its entirety, by reference.

The active compounds are useful in the treatment of animals, including humans, having a broad spectrum of bacterial infections, particularly gram-positive bacterial strains.

The active compounds may be administered alone, but will generally be administered in a mixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of about 5 to about 5000 ppm, preferably about 25 to about 500 ppm. They can be injected parenterally, for example, intramuscularly, intravenously or subcutaneously, For parenteral administration, they are best used in the form of a sterile aqueous solution which can contain other solutes, for example, enough salt or glucose to make the solution isotonic. In the case of animals, the compounds of formula I can be administered intramuscularly or subcutaneously at dosage levels of about 0.1 to about 50 mg/kg/day, advantageously about 0.2 to about 10 mg/kg/day given in a single daily dose or up to 3 divided doses.

The active compounds can be administered to humans, for the treatment of bacterial diseases, by either oral or parenteral routes, and may be administered orally at dosage levels of about 0.1 to 500 mg/kg/day, advantageously 0.5–50 mg/kg/day given in a single dosage or up to 3 divided dosages. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations, in dosages, will necessarily occur depending on the weight and condition of the subject being treated and the particular route of administration chosen as will be known to those skilled in the art.

The antibacterial activity of the active compounds is determined by testing according to the Steer's replicator technique which is a standard in vitro bacterial testing method described by E. Steers et al., Antibiotics and Chemotherapy, 9, 307 (1959).

The following examples illustrate the methods and intermediates useful in the practice of the present invention. It will be understood, however, that the invention is not limited to the specific details of these examples.

EXAMPLE 1

Tetrabutylammonium 2,6-di-t-butylphenoxide

A solution of 22.69 g (110 mmol, 1.1 equivalents) of 2,6-di-t-butylphenol in 10 mL of toluene was treated with 100 mL (100 mmol) of a 1M solution of tetrabutylammonium hydroxide in methanol under nitrogen with stirring at ambient temperature. The resulting dark green solution was stirred for 1 hour and concentrated under vacuum to a thick residue. Two 100 mL portions of toluene were added and removed by evaporation under vacuum yielding 52.08 g of wet, crude title compound as a green solid which was used in the next step without further purification. $^1$H NMR (CDCl$_3$) δ 7.13 (d, J=9 Hz, 2H), 6.77 (t, J=9 Hz, 1H), 3.30 (m, 8H), 1.61 (m, 8H), 1.41 (s, 18H), 1.40 (m, 8H), 0.96 (t, J=7 Hz, 12H).

EXAMPLE 2

(1α, 5α, 6α, )-3-Benzyl6-nitro-2,4dioxo-3-azabicyclo[3.1.0]hexane

A stirred mixture of 9.4 g of 4A bead molecular sieves, 9.4 g of dry Celite, (trademark), 5.62 g (30 mmol) of N-benzylmaleimide, and 120 mL of dry toluene under nitrogen was cooled to −19° C. and treated with 2.7 mL (3.9 mmol, 1.3 equivalents) of bromonitromethane. Tetrabutylammonium 2,6-di-t-butylphenoxide, the title product of Example 1, 23.38 g, was added, via a solid addition funnel, over 1.75 hours to the stirred reaction mixture at −19° C. After 15 minutes of further stirring, the reaction mixture was warmed to −1° C. and treated with 60 mL of 2N hydrochloric acid with vigorous stirring. The mixture was stirred for 1 hour and filtered through a Celite pad. The filtered solids were washed two times with 100 mL of toluene and the combined toluene solutions were washed two times with 60 mL of 2N hydrochloric acid, two times with 50 mL of water and once with brine. The resulting solution was stirred with 3.0 g of Darco (trademark) KBB overnight and filtered. The recovered Darco was washed two times with 50 mL of toluene, the toluene solutions were combined and the toluene was removed under vacuum to yield 14.95 g of a partially solidified orange-brown oil. This material was dissolved in 30 mL of toluene at 50° C. The toluene was removed by distillation under reduced pressure at 50° C., using a heated oil bath, while maintaining a constant volume by adding a total of 120 mL of isopropanol. This resulting slurry was stirred at 50° C. for 3 hours. Heating of the mixture was discontinued and the mixture was allowed to slowly cool to room temperature overnight. The mixture was then cooled to 0° C. for 3 hours and filtered. The filtered solids were washed with 10 mL of cold isopropanol followed by hexanes, and dried under vacuum giving 3.07 g (42% yield) of the title compound as a light tan solid.

mp 108–109° C. $^1$H NMR (CDCl$_3$) δ 7.31 (m, 5H), 4.53 (s, 2H), 4.49 (t, J=1.6 Hz, 1H), 3.35 (d, J=1.6 Hz, 2H).

I claim:

1. A process for preparing a compound of the formula

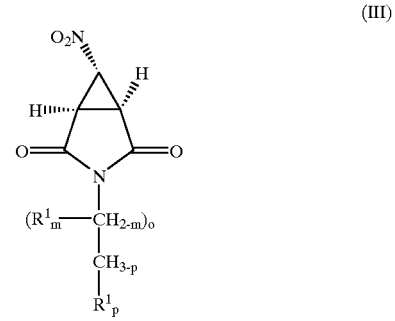

(III)

wherein each $R^1$ is independently selected from hydrogen, optionally substituted ($C_1$–$C_6$)alkyl or optionally substituted ($C_6$–$C_{10}$)aryl wherein said substituents independently are attached to the maximum allowable number of carbon atoms and are each independently selected from halo, nitro, ($C_1$–$C_6$) alkyl, ($C_1$–$C_6$) alkoxy, amino and trifluoromethyl or two $R^1$ groups together with the carbon atom to which they are attached form a ($C_3$–$C_8$)cycloalkyl ring;

o is 0 or an integer from 1 to 5;

m is 0, 1 or 2; and p is 0 or an integer from 1 to 3;

which comprises adding a compound of the formula

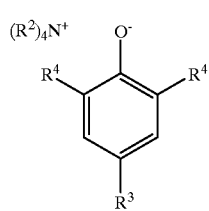

(IV)

wherein each $R^2$ may be different and is independently selected from the group comprising $(C_1-C_{16})$alkyl and benzyl;

$R^3$ is selected from the group described for $R^1$; and each $R^4$ may be different and is independently selected from $(C_1-C_6)$alkyl wherein said alkyl group may be a straight chained hydrocarbyl group or, if consisting of more than two carbon atoms may also be branched or cyclic; to a solution comprising a compound of the formula

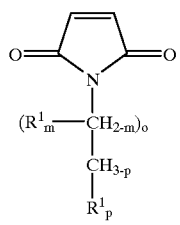

II wherein $R^1$, m, o and p are as described above, and a halonitromethane, of the formula $O_2NCH_2X$ wherein X is a halogen atom dissolved in a non-aqueous solvent.

2. The process according to claim 1 wherein at least one $R^4$ is a branched $(C_4-C_6)$alkyl group.

3. The process according to claim 1 wherein each $R^4$ is a branched $(C_4-C_6)$alkyl group.

4. The process according to claim 1 wherein said compound is tetrabutylammonium 2,6di-t-butyl phenoxide.

5. The process according to claim 1, wherein said halonitromethane is bromonitromethane or chloronitromethane.

6. The process according to claim 1, wherein said process is carried out at a temperature from about −78° C. to about 80° C.

7. The process according to claim 6 wherein said temperature is from about −17 to about −19° C.

8. The process according to claim 1 wherein said inert solvent is selected from benzene, toluene, dimethylformamide, dimethylacetamide, dimethylsulfoxide, ethyl ether, glyme and tetrahydrofuran and mixtures thereof.

9. The process according to claim 8 wherein said solvent is toluene.

10. The process according to claim 1 wherein the reaction is carried out in an inert atmosphere.

11. The process according to claim 1 wherein the reaction is carried out in the presence of a solid support.

12. The process according to claim 11 wherein said solid support is selected from molecular sieves, diatomaceous earth and mixtures thereof.

13. The process according to claim 12 wherein said solid support consists of a mixture of bead molecular sieves and diatomaceous earth.

* * * * *